US00PP09522P

United States Patent [19]

Schumann et al.

[11] Patent Number: Plant 9,522

[45] Date of Patent: Apr. 23, 1996

[54] GERANIUM PLANT NAMED 'FISUNA'

[75] Inventors: Ingeborg Schumann, Albstadt; Angelika Utecht, Montabaur, both of Germany

[73] Assignee: Florfis AG, Binningen, Switzerland

[21] Appl. No.: 360,645

[22] Filed: Dec. 21, 1994

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Foley & Lardner

[57] ABSTRACT

A new and distinct cultivar of geranium plant named Fisuna, particularly characterized by the combined features of white semi-double flowers, intense green foliage with weak zonation, vigorous growth and medium spring flower response.

1 Drawing Sheet

The present invention comprises a new and distinct cultivar of geranium, botanically known as *Pelargonium peltatum l'Hert*, commonly referred to as ivy geranium, and referred to by the cultivar name Fisuna.

Fisuna was originated from a hybridization made by inventor Ingeborg Schumann in a controlled breeding program in Galdar, Gran Canaria, Spain in 1987. The female parent was a hybrid produced from a cross between a chance seedling of the cultivar Rigi, and the cultivar Martine. Rigi has large pink flowers and vigorous but loose growth habit. Martine has single red flowers, foliage with zonation, and medium growth. The male parent was the commercial cultivar Pink Charme, a cultivar having light salmon pink flowers, foliage with strong zonation, and medium growth.

Fisuna was discovered and selected as one flowering plant within the progeny of the stated cross by Ingeborg Schumann in 1988 in a controlled environment in Galdar, Gran Canaria, Spain.

The first act of asexual reproduction of Fisuna was accomplished when vegetative cuttings were taken from the initial selection in autumn 1990 in a controlled environment in Galdar, Gran Canaria, Spain by, or under the supervision of, Angelika Utecht.

Horticultural examination of plants grown from these cuttings initiated in May 1991, and continuing thereafter, has demonstrated that the combination of characteristics as herein disclosed for Fisuna are firmly fixed and are retained through successive generations of asexual reproduction.

Fisuna has not been observed under all possible environmental conditions. The phenotype may vary significantly with variations in environment such as temperature, light intensity and daylength without, however, any variation in genotype. The following observations, measurements, and comparisons describe plants grown in Hillscheid, Federal Republic of Germany under greenhouse conditions which approximate those generally used in commercial practice.

The following traits have been repeatedly observed and are determined to be basic characteristics of Fisuna, which, in combination, distinguish this geranium as a new and distinct cultivar:

1. White semi-double flowers.
2. Intense green leaves with weak zonation.
3. Vigorous growth habit.
4. Medium spring flower response.

Of the many commercial cultivars known to the inventors, the most similar in comparison to Fisuna is the commercial cultivar Snow Queen. Reference is made to attached Chart A which compares certain characteristics of Fisuna to those same characteristics of Snow Queen. In general comparison to Snow Queen, Fisuna has more intense green foliage without any tendency to yellow, smaller flowers, and a more floriferous habit. The white flower color and markings are similar in both cultivars.

The accompanying color photographic drawing shows typical flower and foliage characteristics of Fisuna, with colors being as true as possible with illustrations of this type.

In the following description, color references are made to The Royal Horticultural Society Colour Chart. The color values were determined indoors in May from plants grown indoors in Hillscheid, Federal Republic of Germany.

Classification:

*Botanical.*—A hybrid of the species *Pelargonium peltatum l'Hert.*

*Commercial.*—Ivy geranium, cv., Fisuna.

INFLUORESCENCE

Umbel:

*Shape.*—Umbrella-shaped, very flat semi-spherical.

*Average diameter.*—100 mm.

*Average depth.*—40 mm.

*Peduncle length.*— 200 mm.

*Pedicel length.*—30 mm.

*Pedicel color.*—Green, with a little anthocyanin.

*Number of flowers per umbel.*—8–9.

Corolla:

*Average diameter.*—48 mm.

*Form.*—Semi-double.

*Number of petals.*—11.

*Number of petaloids.*—2.

*Color (general tonality from a distance of three meters).*—White, with young flowers sometimes having a slight pink shade.

*Color of upper petals.*—155D.

*Color of lower petals.*—155D, with very weak purple streaking on upper side of petals but not visible on under surface.

*Markings on upper petals.*—There are purple veins and two purple streaks running from the base of the petal to about the middle of the petal. A spot of the same color is between and connects the upper ends of these streaks.

*Color of under surface of upper petals.*—155D; the purple streaks referred to are also visible on the under surface but they are lighter and diminish near the upper end.

*Color of sepals.*—Green, largest petal has very weak anthocyanin color.

*Number of sepals.*—5–6.

Bud:

*Shape.*—Narrow, elliptical.

*Color (adaxial).*—Green.

*Color (abaxial).*—Cream colored or very light pink.

Reproduction organs:

*Androecium.*—2–5 fertile anthers, white filaments, orange pollen.

*Gynoecium.*—5–6 lobed stigma, white style and purple pink stigma.

Spring flowering response period: In Hillscheid, Federal Republic of Germany, in 1993 plants had on average 0.9 flowers opened 15 weeks after planting of unrooted cuttings (pinched plants).

Outdoor flower production: The flower count in 1993 in Hillscheid, Federal Republic of Germany was between 45 and 50 umbels per plant for May through August observation period.

Durability: Shatter resistance good.

Seed: Seed set seldom observed and never affects flowering.

PLANT

Foliage:

*Form.*—Ivy shaped, smooth glossy surface.

*Margin.*—Entire.

*Size of leaf.*—90 mm.

*Color of upper surface.*—Medium green, approximately 137B–C.

*Color (zonation).*—Brown 166A. Zoning is inconspicuous and may not be seen in all leaves in all seasons; oldest leaves generally show heaviest degree of zoning.

*Tolerance of botrytis.*—Good, due to smooth surface.

General appearance and form:

*Internode length.*—50–60 mm.

*Branching pattern.*—2.4 branches per week.

*Length.*—90 cm (in Septemper, 35-week-old plants).

CHART A

| CHARACTERISTIC | FISUNA | SNOW QUEEN |
|---|---|---|
| Flower color | White | White |
| Flowers per umbel | 8–9 | 5 |
| Peduncle diameter | 2–2.5 mm | 3 mm |
| Leaf color | 137B–C | 137C–D |

It is claimed:

1. A new and distinct cultivar of geranium plant named Fisuna, as illustrated and described.

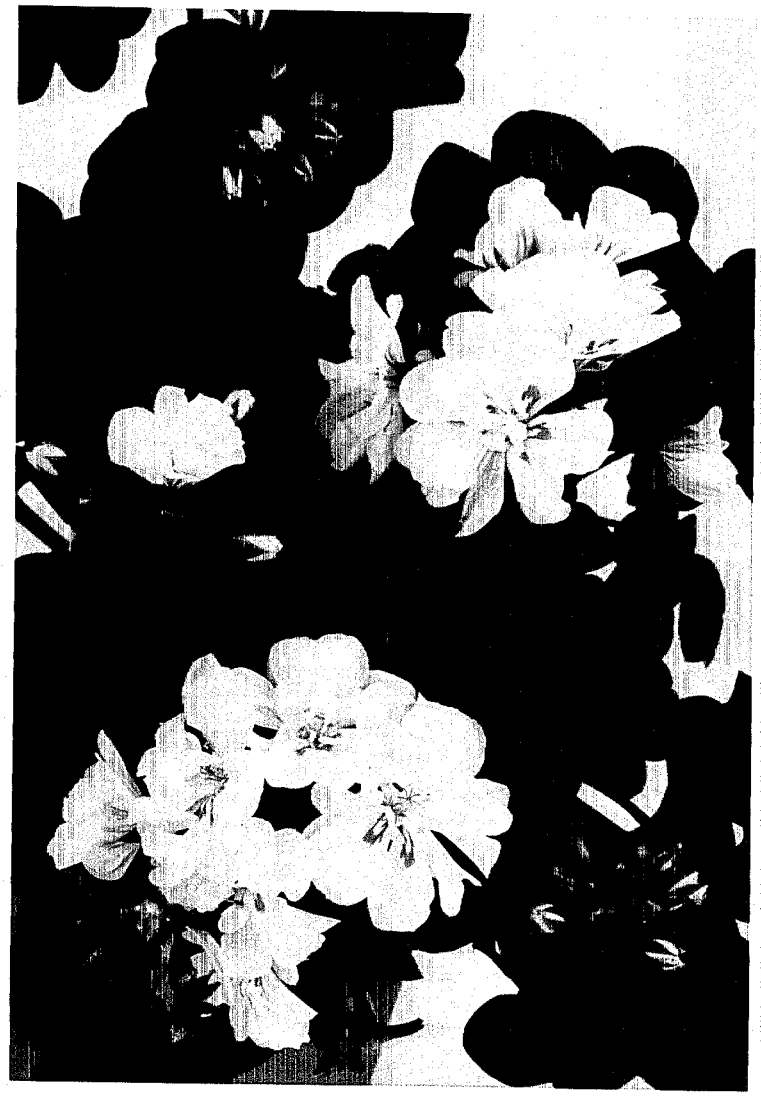

* * * * *